US008931388B2

(12) United States Patent
Jezierski

(10) Patent No.: US 8,931,388 B2
(45) Date of Patent: Jan. 13, 2015

(54) CUTTING TOOL HAVING A MAGNETICALLY CONTROLLED PRE-LOAD FORCE

(75) Inventor: Rafal Z. Jezierski, Wilmington, MA (US)

(73) Assignee: Smith & Nephew, Inc., Memphis, TN (US)

( * ) Notice: Subject to any disclaimer, the term of this patent is extended or adjusted under 35 U.S.C. 154(b) by 394 days.

(21) Appl. No.: 11/566,738

(22) Filed: Dec. 5, 2006

(65) Prior Publication Data
US 2008/0132928 A1    Jun. 5, 2008

(51) Int. Cl.
*A61B 17/32* (2006.01)
*A61B 17/00* (2006.01)

(52) U.S. Cl.
CPC . *A61B 17/32002* (2013.01); *A61B 2017/00876* (2013.01)
USPC ............... 83/698.21; 83/698.11; 606/171; 606/167

(58) Field of Classification Search
USPC .......................... 83/13, 679, 698.11, 698.21; 606/169–171, 167, 180; 464/29, 160, 464/161; 403/DIG. 1; 74/22 R, 23
See application file for complete search history.

(56) References Cited

U.S. PATENT DOCUMENTS

| | | |
|---|---|---|
| 5,077,506 A | 12/1991 | Krause |
| 5,275,607 A | 1/1994 | Lo et al. |
| 5,593,415 A * | 1/1997 | Adrian ......................... 606/169 |
| 6,478,681 B1 * | 11/2002 | Overaker et al. ............... 464/29 |
| 6,629,986 B1 | 10/2003 | Ross et al. |
| 6,689,146 B1 * | 2/2004 | Himes ........................... 606/167 |
| 2001/0007944 A1 * | 7/2001 | Mark et al. .................... 606/170 |
| 2002/0072033 A1 | 6/2002 | Bierbaum et al. |
| 2007/0142780 A1 | 6/2007 | Van Lue |

FOREIGN PATENT DOCUMENTS

| | | |
|---|---|---|
| DE | 4414903 | 11/1995 |
| EP | 1362559 | 11/2003 |
| JP | 02-009515 | 1/1990 |
| JP | H05-029509 | 9/1991 |
| JP | H05-045239 | 11/1991 |
| JP | H05-029509 | 4/1993 |
| JP | 2000-000246 | 1/2000 |
| WO | WO 93/05718 | 4/1993 |
| WO | 94/06681 A | 3/1994 |
| WO | 9639957 | 12/1996 |

(Continued)

OTHER PUBLICATIONS

International Search Report and Written Opinion for PCT/US2007/085862 Dated Oct. 14, 2008.

(Continued)

*Primary Examiner* — Phong Nguyen
(74) *Attorney, Agent, or Firm* — Norman F. Hainer, Jr.

(57) ABSTRACT

A cutting tool includes an outer tubular member having a first magnet and an inner tubular member having a second magnet wherein the inner tubular member is slidably disposed within the outer tubular member. A force, such as an attractive or opposing force, is created between the first magnet and the second magnet. The attractive or opposing force creates a preload force between the inner tubular member and the outer tubular member or a hand piece that is engaged with the inner tubular member. A method of creating a force between an inner and outer tubular member is also disclosed.

40 Claims, 7 Drawing Sheets

(56) References Cited

FOREIGN PATENT DOCUMENTS

| WO | WO99/13790 | 3/1999 |
|---|---|---|
| WO | WO 99/13790 A | 3/1999 |
| WO | 0241788 | 5/2002 |
| WO | WO2005/048814 A2 | 6/2005 |
| WO | 2008082826 | 7/2008 |

OTHER PUBLICATIONS

Office Action for European Patent Application EP 07-871-642.0-2310 mailed Jul. 8, 2010.
First Office Action regarding Chinese Patent Application No. 200980128775.4 mailed Oct. 23, 2012.
First Office Action regarding Japanese Patent Application No. 200980128775.4 mailed Oct. 31, 2012.
Office Action for corresponding JP Application No. 2009-540390 mailed Feb. 26, 2013.
Office Action for corresponding EP application No. 09751105.9-1506 mailed Nov. 22, 2013.
Office Action for corresponding JP application No. 2011-510542 mailed Aug. 13, 2013.
Office Action for corresponding JP application No. 2009-540390 mailed Oct. 22, 2013.
Office action received in corresponding Australian application No. 2009249477 mailed Sep. 20, 2013.
Office action received in corresponding Australian application No. 2007340189 mailed Dec. 20, 2013.
Office action received in corresponding Japanese patent application No. 2009-540390 mailed May 26, 2014.
Office action received in corresponding Japanese application No. 2011-518863 dated Feb. 18, 2014.
First Office Action regarding Australian Patent Application No. 2007340189 mailed Jun. 1, 2012.
First Office Action regarding Japanese Patent Application No. 2009-540390 mailed Aug. 17, 2012.

\* cited by examiner

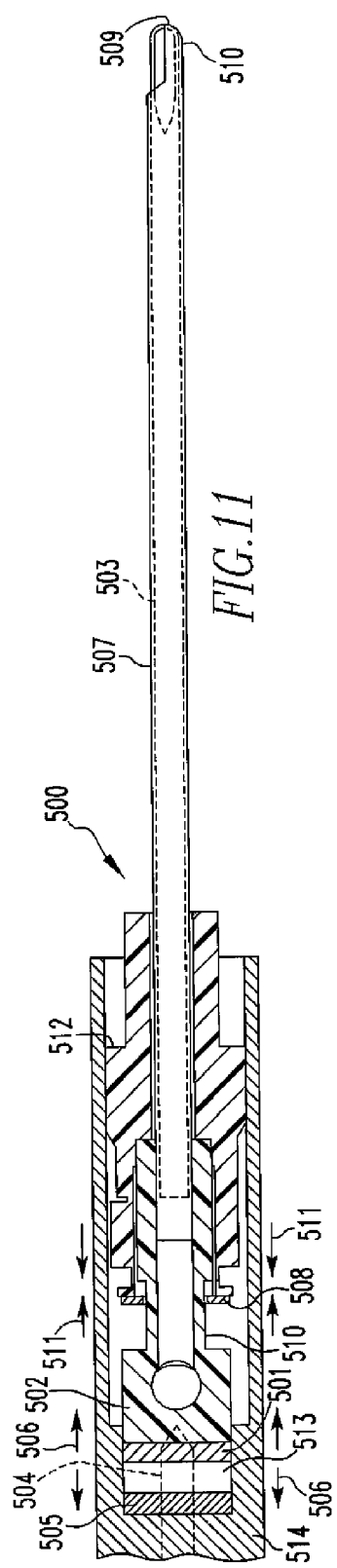
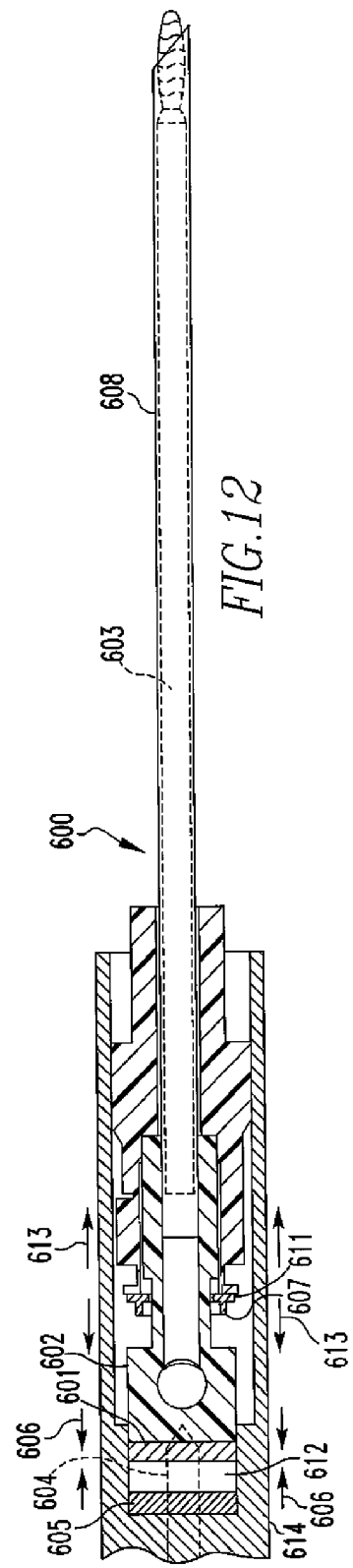

CUTTING TOOL HAVING A MAGNETICALLY CONTROLLED PRE-LOAD FORCE

BACKGROUND OF THE INVENTION

1. Field of the Invention

The present disclosure relates to cutting tools and, more particularly, to surgical cutting instruments having elongate, inner and outer tubular members with distal ends cooperating to cut or resect bodily tissue.

2. Related Art

Elongate surgical cutting tools have been used in performing closed surgery, such as endoscopic surgery, i.e. arthroscopic surgery. FIG. 1 shows a surgical cutting instrument 10 for use in closed surgery. The cutting instrument 10 has an elongate outer tubular member 11 terminating at a distal end 12 having an opening 13 in the side wall and/or the end wall to form a cutting port or window and an elongate inner tubular member 20 (FIG. 2) coaxially disposed in the outer tubular member 11 and having a distal end 21 disposed adjacent the opening 13 in the distal end 12 of the outer tubular member 11. The distal end 21 of the inner tubular member 20 has a surface or edge 22 for engaging tissue via the opening 13 in the distal end 12 of the outer tubular member 11 and in many cases cooperates with the opening 13 to shear or cut tissue. A vacuum source (not shown) is coupled to the cutting instrument 10 and vacuums the tissue, and the irrigating fluid surrounding the tissue, out of the instrument 10. The outer and inner tubular members 11,20 each have a plastic hub 15,24 at their proximal ends 14,23. The hub 24 of the inner tubular member 20 has a transversely extending passage 25 therethrough, the inner tubular member 20 extending through an axial bore 26 in the hub 24 to communicate with the passage 25. A drive tang 27 within portion 28 is adapted to be driven via a hand piece (not shown) having a small electric motor therein controlled by finger-actuated switches on the hand piece. A foot switch or switches on a console supply power to the hand piece. FIGS. 1 and 2 represent components of a cutting instrument known in the industry as an end-bearing cutting instrument.

FIGS. 3 and 4 represent components of a cutting instrument known in the industry as a burr cutting instrument. The burr cutting instrument 30 also has an elongate outer tubular member 31 terminating at a distal end 32 having an opening 33 in the side wall and/or the end wall to form a cutting port or window and an elongate inner tubular member 40 (FIG. 4) coaxially disposed in the outer tubular member 31 and having a distal end 41 disposed adjacent the opening 33 in the distal end 32 of the outer tubular member 31. The distal end 41 of the inner tubular member 40 has a helical grooved surface or edge 42 for drilling and grinding tissue via the opening 33 in the distal end 32 of the outer tubular member 31 and in many cases cooperates with the opening 33 to shear or cut tissue. The inner tubular member 40 is likewise rotatably driven at its proximal end 43, normally via a hand piece having a small electric motor therein controlled by finger-actuated switches on the hand piece. A foot switch or switches on a console supply power to the hand piece.

Currently, the designs of both the end-bearing and burr cutting instruments utilize either a compression spring and a housing assembly (28,45) integrated into the inner tubular member (20,40) or a compression spring integrated into the driveshaft assembly of the hand piece unit (not shown). When a compression spring and a housing assembly 28 are integrated into the inner tubular member 20, the outer tip surface 29 of the inner tubular member 20 is preloaded against the inner tip surface 16 of the outer tubular member 11 in the case of end-bearing cutting instruments. Burr cutting instruments utilize a thrust washer 34 to preload the inner tubular member 40 against the outer tubular member 31, as there is no contact between the inner and the outer tip surfaces (46,35). The thrust washer 34 is a circular-shaped piece of polymer material. However, the washer 34 could be of another shape or type of material.

With either cutting instrument, the preload force is only generated once the cutting instrument is engaged in the hand piece unit. The preload force is the force involved in preloading components, such as the inner and outer tubular members, against one another. The amount of preload is dependent on the dimensional variation of the cutting instrument components and the hand piece unit. There are no means of retention of the inner tubular member within the outer tubular member unless the cutting instrument is engaged in the hand piece. In addition, the thrust washer arrangement makes the burr cutting instruments susceptible to excessive shedding and seizing. In use, the hand piece unit drives the inner tubular member against the outer tubular member, and especially in burr instruments, the washer breaks down and small pieces of shredded material from the washer become lodged in the drive tang/hand piece connection and, in some cases, inhibit the vacuum from suctioning the tissue and irrigating fluid. When this happens, the interface of the drive tang/hand piece, due to an insufficient amount of fluid in this area, may overheat causing seizing of the drive tang/hand piece and possible melting of the drive tang.

When a compression spring is integrated into the driveshaft assembly of a hand piece unit, there are no inner tubular member retention issues when the cutting instrument is disengaged from the hand piece unit. As shown in FIG. 5, a retainer 51 is integrated into the hub outer tubular member 50 to retain the inner tubular member 62 (FIG. 6) in the outer tubular member 52. In addition, as shown in FIG. 6, the inner tubular member 62 has a groove 63 at its proximal end 64 that the retainer 51 rests in to retain the inner tubular member 62 when the inner tubular member 62 is disposed into the outer tubular member 52. The tool that is shown in FIGS. 5 and 6 is an end-bearing cutting tool. However, a retainer can also be used with a burr cutting tool. The design of having the compression spring integrated into the driveshaft assembly is not feasible in small diameter cutting instrument applications due to size limitations of the compression spring and driveshaft.

A cutting instrument is needed whereby the preload force can be controlled more precisely. In addition, a cutting instrument having a design that avoids having to take into account the physical limitations of the driveshaft unit is needed. Furthermore, a cutting instrument that is simpler and less costly to make is also needed. Finally, a burr cutting instrument is needed that does not depend on the use of a thrust washer.

SUMMARY OF THE INVENTION

The present disclosure relates to a cutting tool that includes an outer tubular member having a first magnet and an inner tubular member having a second magnet wherein the inner tubular member is slidably disposed within the outer tubular member. A force is created between the first magnet and the second magnet when the inner tubular member is slidably disposed within the outer tubular member. The force may be an attractive force or an opposing force. In an embodiment, the attractive force creates a preload force between the inner tubular member and the outer tubular member. In another embodiment, the opposing force creates a preload force between the inner tubular member and a driveshaft when the inner tubular member and the driveshaft are engaged. The first magnet and the second magnet are coupled to the outer and inner tubular members. In an embodiment, the first magnet and the second magnet are coupled to hubs of the inner and outer tubular members. The polarities of the first and second magnets may be the same or different. An air gap of between about 0.001 inches and about 0.300 inches exists between the first magnet and the second magnet.

In an embodiment, the inner and outer tubular members both include magnetic material. In another embodiment, the outer tubular member comprises a retention feature that creates a coupling between the outer tubular member and the inner tubular member.

In yet another embodiment, a surgical cutting instrument is disclosed. The surgical cutting instrument includes an outer tubular member including a first magnet and an inner tubular member including a second magnet, wherein the inner tubular member is slidably disposed within the outer tubular member. A force is created between the first magnet and the second magnet when the inner tubular member is slidably disposed in the outer tubular member.

A method of creating a force between an outer tubular member and an inner tubular member of a cutting tool is also disclosed. The method includes coupling a first magnet to an outer tubular member, coupling a second magnet to an inner tubular member, and slidably disposing the inner tubular member within the outer tubular member to create a force between the outer tubular member and the inner tubular member. The first and second magnets may be coupled to hubs of the outer and inner tubular members. Coupling the first magnet to the outer tubular member and the second magnet to the inner tubular member includes mechanical coupling, magnetic coupling, or bonding.

A further alternate embodiment includes an outer tubular member and an inner tubular member including a magnet, wherein the inner tubular member is slidably disposed within the outer tubular member. A force is created between the magnet of the inner tubular member and a magnet of a hand piece upon engagement of the inner tubular member and the hand piece. The force includes an opposing force or an attractive force. In an embodiment, the opposing force creates a preload force between the inner tubular member and the outer tubular member. In another embodiment, the attractive force creates a preload force between the inner tubular member and the hand piece. The cutting tool may include a magnet on the outer tubular member that has a same polarity from the magnet on the inner tubular member. In addition, the outer tubular member may include a retention feature that creates a coupling between the outer tubular member and the inner tubular member. An air gap of between about 0 inches to about 0.300 inches exists between the magnet of the inner tubular member and the magnet of the hand piece.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings:

FIG. 11 shows a cross-sectional view of another embodiment of an end-bearing cutting tool of the present disclosure.

FIG. 12 shows a cross-sectional view of another embodiment of a burr cutting tool of the present disclosure.

DETAILED DESCRIPTION OF THE EMBODIMENTS

The following description of the preferred embodiments) is merely exemplary in nature and is in no way intended to limit the invention, its application, or uses.

Figure 1:
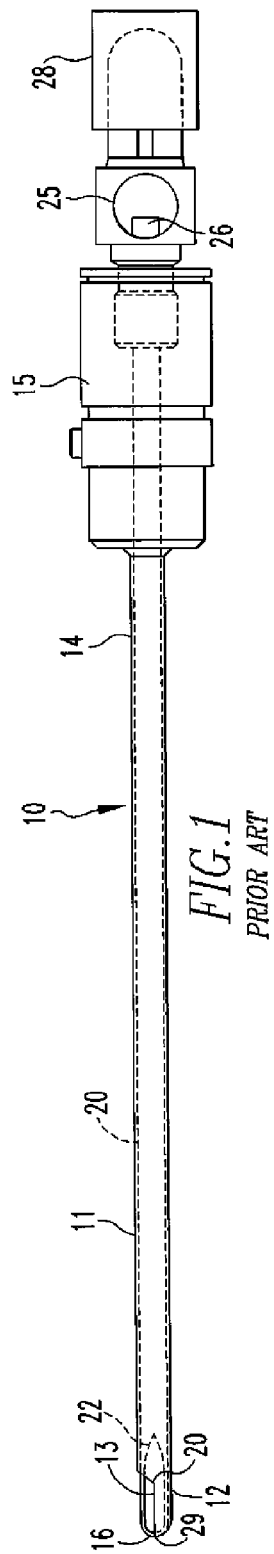
FIG. 1 shows an embodiment of a surgical cutting tool.
Figure 2:
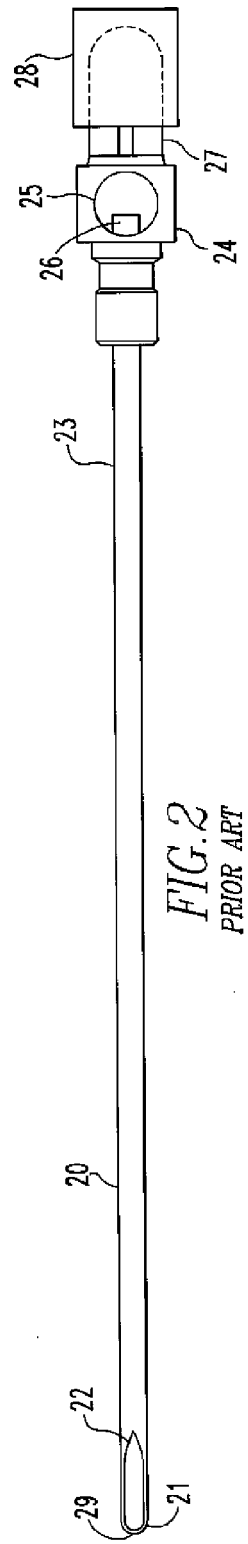
FIG. 2 shows an inner tubular member of the surgical cutting tool shown in FIG. 1
Figure 3:
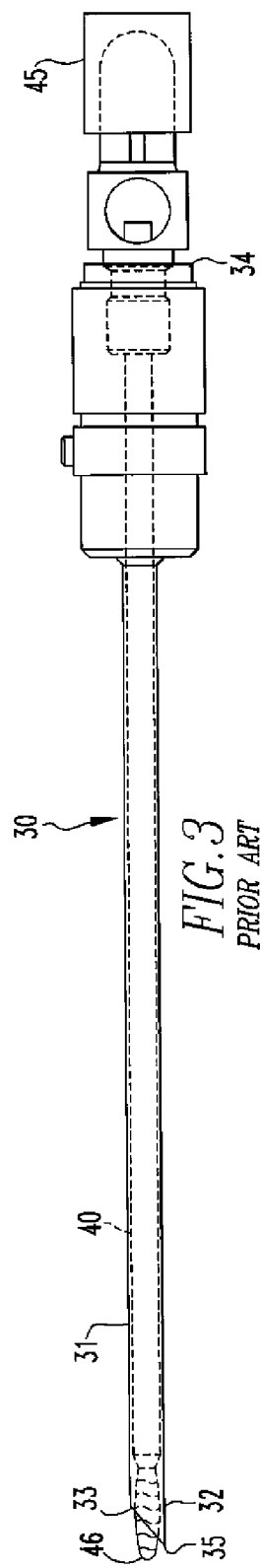
FIG. 3 shows another embodiment of a surgical cutting tool.
Figure 4:
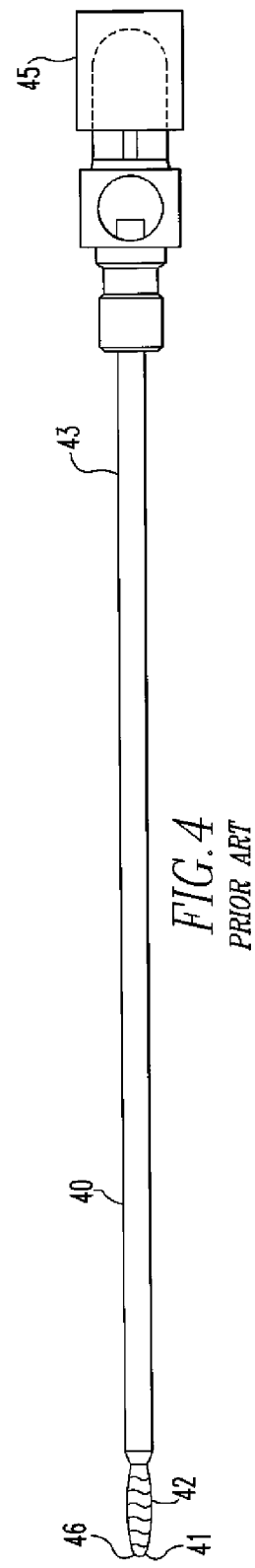
FIG. 4 shows an inner tubular member of the surgical cutting tool shown in FIG. 3.
Figure 5:
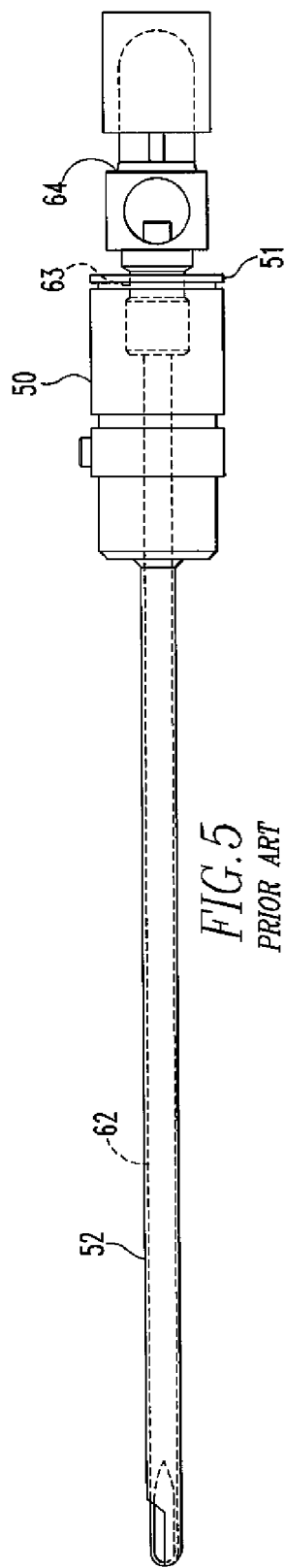
FIG. 5 shows a retention ring of an outer tubular member of a surgical cutting instrument.
Figure 6:
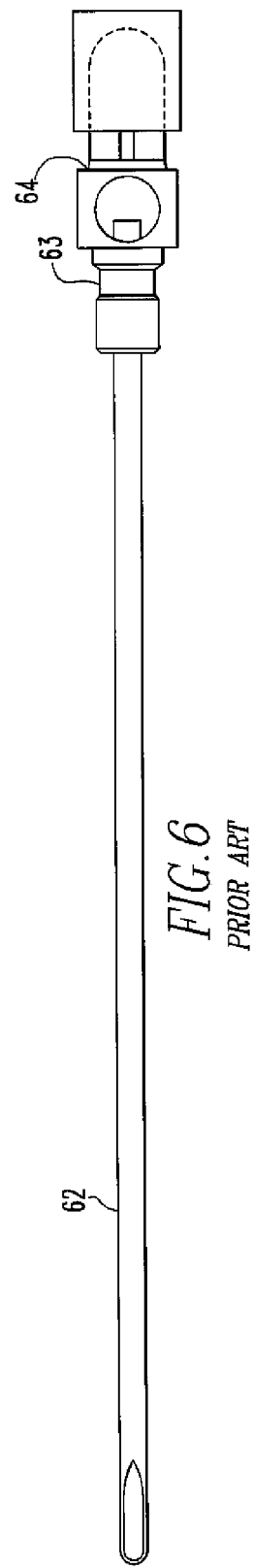
FIG. 6 shows a groove in the proximal end of an inner tubular member of a surgical cutting instrument.
Figure 7:
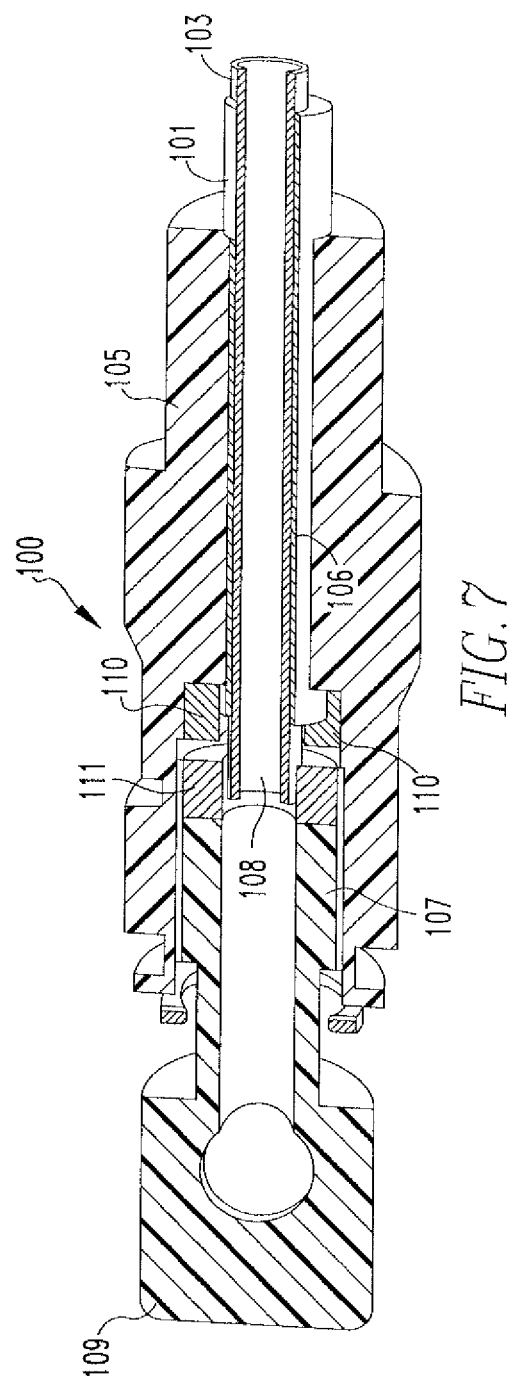
FIG. 7 shows a cross-sectional view of the cutting tool of the present disclosure.

FIG. 7 shows a cross-sectional view of the cutting tool 100 of the present disclosure. The tool 100 includes an outer tubular member 101 and an inner tubular member 103. Both the outer tubular member 101 and the inner tubular member 103 include a hub 105,107 coupled to the proximal end 106, 108 of the tubular members 101,103. The tubular members 101,103 include a metal material, such as steel or stainless steel, and the hubs 105,107 are molded from a polymer material. The inner tubular member 103 is slidably disposed within the outer tubular member 101 so as to align the distal ends of the outer and inner tubular members 101,103, as described above and shown in FIGS. 8 and 9. Alignment of the distal ends allows the outer and inner tubular members 101,103 to cut or resect tissue when a drive tang 109 of the inner tubular member 103 is driven via a hand piece (not shown), as described above. The outer tubular member 101 includes a first magnet 110 and the inner tubular member 103 includes a second magnet 111. The magnets 110,111 are coupled to the outer and inner tubular members 101,103. However, the magnets 110,111 may be coupled to the hubs 105,107 of the tubular members 101,103. The first magnet 110 and the second magnet 111 create a force between the outer tubular member 101 and the inner tubular member 103. The magnets used in this disclosure are permanent magnets. However, other types of magnets known to those skilled in the art may be used.

Figure 8:
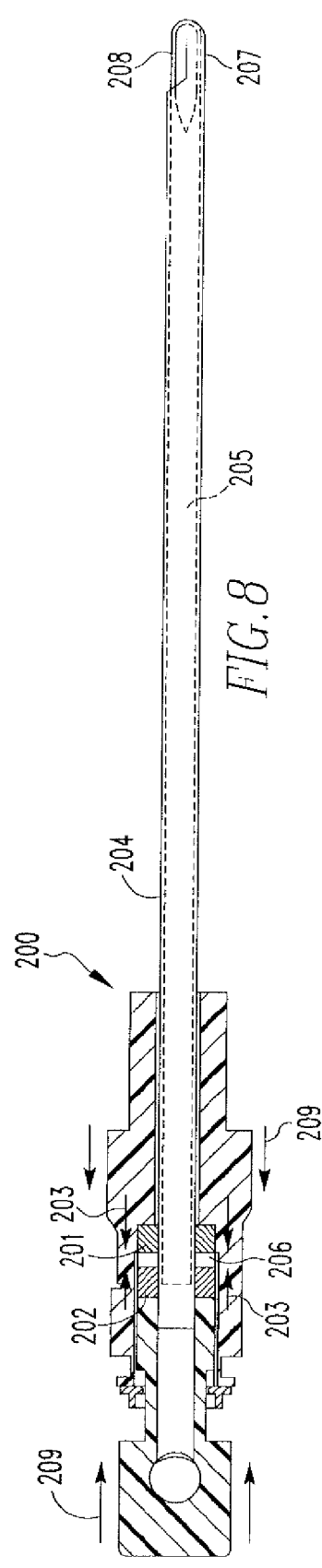
FIG. 8 shows a cross-sectional view of an end-bearing cutting tool of the present disclosure.

When used in an end-bearing cutting tool 200, as shown in FIG. 8 and as described above, the magnets 201, 202 are arranged to create an attracting force, 203, between the first magnet 201 and the second magnet 202. The attractive force 203, which is due to the magnets having different polarities, creates a preload force 209 between the outer and inner tubular members 204,205. Possible configurations include a magnet 201 on the outer tubular member 204 having its south pole lacing the north pole of a magnet 202 on the inner tubular member 205 and vice versa. An air gap 206 also exists between the magnets 201, 202. This air gap 206 ensures that the outer surface tip 208 of the inner tubular member 205 contacts the inner surface tip 207 of the outer tubular member 204. Assuming fixed physical properties of the magnets 201, 202, the preload force that is created between the inner tubular member 205 and the outer tubular member 204 is dependent on the polarity of the magnets 201,202 and the air gap 206 between them. The dimensional variation of the hand piece components has no impact on the amount of preload, thus the preload force can be controlled more precisely. In addition, an inner tubular member retention feature is not necessary, as the cutting tool is in its preloaded state whether or not it is engaged in the hand piece unit. This allows for a simplified huh and seal design for the outer tubular member.

Figure 9:
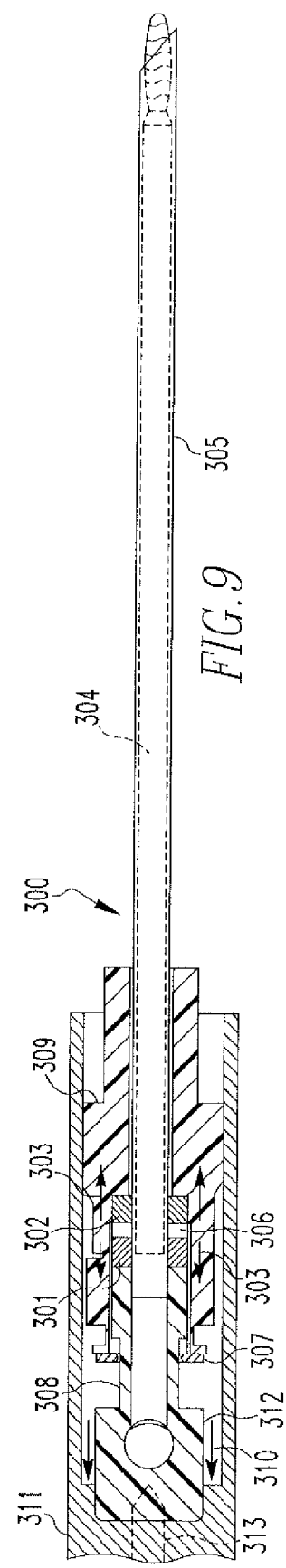
FIG. 9 shows a cross-sectional view of a burr cutting tool of the present disclosure.

When used in a burr cutting tool 300, as shown in FIG. 9 and as described above, an opposing force 303 is created between the magnets 301, 302. The opposing force 303 creates a preload force 310 between the inner tubular member 304 and a driveshaft 313 of a hand piece 311 when the driveshaft 313 and a hub 312 of the inner tubular member 304 are engaged. The opposing force 303 is due to the magnets having the same polarity. Possible configurations include both magnets 301,302 having their south poles or north poles facing one another. An air gap 306 also exists between the magnets 301,302. The air gap 306 eliminates the need for the thrust washer, as the direction of the preload 310 of the inner tubular member is reversed, i.e. the inner tubular member is preloaded against the hand piece 311 driveshaft 313 instead of the thrust surface of the outer tubular member hub. Elimination of the thrust washer eliminates contact between the inner and outer tubular members, thereby minimizing the risk of shedding and/or seizing. Assuming fixed physical properties of the magnets 301,302, the preload force 310 is dependent on the size of the air gap 306 between the magnet faces.

A retention feature 307, such as a modified o-ring having tabs located on a wall of the o-ring, is necessary as the direction of the opposing 303 force results in the separation of the inner tubular member 304 and the outer tubular member 305. This can be incorporated into the design of the hub 309 of the outer tubular member 305. The inner tubular member 304 has a groove 308 that the retention feature 307 rests in to retain the inner tubular member 304 when the inner tubular member 304 is disposed into the outer tubular member 305. The retention feature may also include the use of sensor magnets incorporated into the material of the hub 309 of the outer tubular member 305. These sensor magnets would have a different polarity from the magnet 301 that is coupled to inner tubular member 304 so as to create an attracting force between the sensor magnets and the inner tubular member magnet 301. However, any retention feature that would retain the inner tubular member within the outer tubular member could be used. The air gap that exists between the magnets in both applications is between about 0.001 inches and about 0.300 inches.

Figure 10:
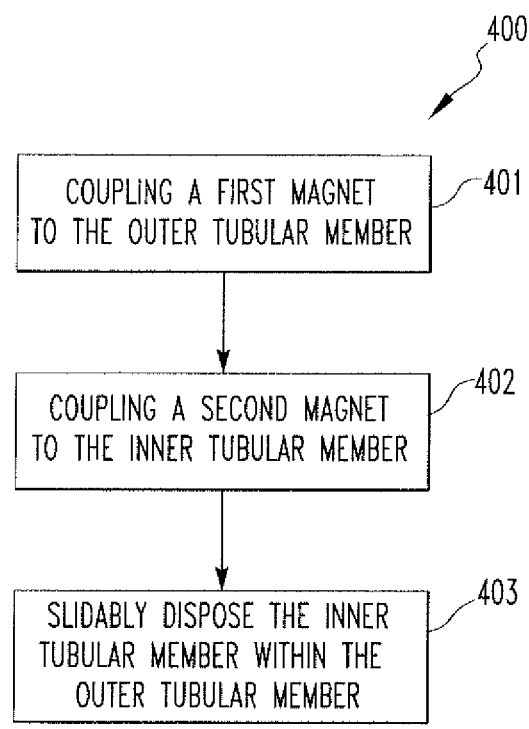
FIG. 10 shows a method of making the cutting instrument of the present disclosure.

As shown in FIG. 10, a method of creating a force between an outer tubular member and an inner tubular member of a cutting tool 400 includes coupling a first magnet to the outer tubular member 401, coupling a second magnet to the inner tubular member 402, and slidably disposing the inner tubular member within the outer tubular member to create a force between the outer tubular member and the inner tubular member 403. The magnets may also be coupled to the hubs of the outer and inner tubular members.

The magnets in the present disclosure are coupled to the hub or member via a biocompatible, non-toxic adhesive glue. Coupling of the magnets may also include mechanical coupling, magnetic coupling, bonding, or embedding the magnets into the hubs of the outer and inner tubular members. Mechanical coupling may include using a snap fit or tab design on the hubs but may include other mechanical means known to those skilled in the art. Magnetic coupling may include coupling the magnets to a hub of either the inner or outer tubular members wherein the hubs are manufactured from a polymer bonded magnetic material having a different polarity from the magnets so as to create an attractive force between the magnet and the magnetic material. In addition, magnetic coupling may also include embedding a component of non-magnetized material, such as metal, into the hub of either tubular member and placing a magnet on the component so as to create a magnetic coupling between the magnet and the member. The magnets may be bonded to the hubs via the above-stated method of adhesive coupling with a biocompatible, non-toxic adhesive glue or via brazing or welding, specifically friction or spin welding. The magnets may also be embedded in the hubs by pressing the magnet into the hub via a customized or industrial press or by molding the magnet into the hub by placing a polymer material and the magnet into a mold and then forming the hub.

An alternative embodiment of the present disclosure includes the use of a polymer bonded magnetic material magnetized to incorporate functionality of individual magnets into molded polymer hub assemblies 105,107 of outer and inner tubular members 101,103 as shown in FIG. 7. Other alternative embodiments include the incorporation of a flexible or compressible member, such as a spring or any other material having resistive or flexible qualities, into the hub of either the inner or outer tubular members, and a pocket of pressurized fluid exerting a preload force on the inner and/or outer tubular members.

Alternative embodiments of using magnets with burr and end-bearing cutting tools are shown in FIGS. 11 and 12. In FIG. 11, an end-bearing cutting tool 500 includes a magnet 501 that is located at the proximal end of the hub 502 of the inner tubular member 503. A hand piece 514 also contains a magnet 505 that is internal or external to the hand piece 514. The magnet 505 of the hand piece 514 and the magnet 501 of the inner tubular member 503 include the same polarities and an opposing force 506 is created between the magnets 501, 505 when the hand piece 514 is placed over the hub 502 in preparation for use of the tool 500. A drive shaft 504 is located within the hand piece 514 and rotatably drives the inner tubular member 503 during use. When the hand piece 514 is connected to the tool 500, a preload force 511 is created between the inner 503 and outer 507 tubular members as the outer tip surface 509 of the inner tubular member 503 is preloaded against the inner tip surface 510 of the outer tubular member 507. A retention feature 508, such as a modified o-ring having tabs located on walls of the o-ring, is necessary to prevent separation of the inner tubular member 503 and the outer tubular member 507 when the tool 500 is not engaged in the hand piece 514. This can be incorporated into the design of the hub 512 of the outer tubular member 507. The inner tubular member 503 has a groove 510 that the retention feature 508 rests in to retain the inner tubular member 503 when the inner tubular member 503 is disposed within the outer tubular member 507. An air gap 513 of between about 0 inches to about 0.300 inches exists between the magnets (501,505).

FIG. 12 shows a burr-cutting tool 600. Similar to the end-bearing cutting tool 500 in FIG. 11, a magnet 601 is located at the proximal end of the hub 602 of the inner tubular member 603. Also as discussed above, a hand piece 614 also contains a magnet 605 that is located external or internal to the hand piece 614. The magnet 605 of the hand piece 614 and the magnet 601 of the inner tubular member 603 include different polarities and an attraction force 606 is created between the magnets 601,605 when the hand piece 614 of the hand piece 614 is placed over the hub 602 in preparation for use of the tool 600. A drive shaft 604 is located within the hand piece 614 and rotatably drives the inner tubular member 603 during use. This attractive force 606 is a preload force between the hand piece 614 and the inner tubular member 603. A magnet 607 may also be included on the outer tubular member 608 to act as a thrust surface against the inner tubular member 603. The magnet 607 includes the same polarity as the magnet 601 of the inner tubular member 603 so as to create an opposing force 613 between the magnets 601,607 and therefore the inner and outer tubular members 603,608. With the orientation of the tool 600 while in use and the fact that there is an attractive force 606 between the magnet 601 of the inner tubular member 603 and the magnet 605 of the hand piece 614 and an opposing force 613 between the magnet 603 of the inner tubular member 603 and the magnet 607 of the outer tubular member 608, it is possible that the inner tubular member 603 would not be thrust against the outer tubular member 608. Therefore, a thrust washer may be used instead of the magnet 607. However, a magnet is still preferred due to the possible shedding of the thrust washer as describe above. Furthermore, a retention feature 611, as described above, may be used to retain the inner tubular member 603 within the outer tubular member 608. An air gap 612 of between about 0 inches to about 0.300 inches exists between the magnets (601,605).

In both of the cutting instruments of FIGS. 11 and 12, the magnets may be coupled to the hand piece and the inner tubular member via the methods as described above. The magnets are permanent magnets, but other types of magnets may also be used.

For the purposes of this disclosure, a magnate that is located external to or internal to the hand piece means that the magnate could be located on the outside surface of the hand piece, within the material of the hand piece, on the inside surface of the hand piece, or on any part that is located inside of the hand piece, including, but not limited to, the drive shaft.

In addition to the above-mentioned advantages of the present disclosure, the cutting tool of the present disclosure reduces the risk of tissue entrapment within the hand piece and therefore reduced hand piece maintenance by not including external components, such as a compression spring and a housing assembly, that are directly in the tissue flow path. Furthermore, the magnets of the present disclosure may be used for inner and outer tubular member configuration identification, thereby expanding the current identification capability.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

I claim:

1. A cutting tool for use with a handpiece, the handpiece including a drive shaft, the cutting tool comprising:
   a one-piece outer tubular member extending from a proximal end of the outer tubular member to a distal end of the outer tubular member, the outer tubular member including a cutting window formed within the distal end of the outer tubular member and a first magnet directly attached to the outer tubular member, the first magnet being a single magnet; and
   a one-piece inner tubular member extending from a proximal end of the outer tubular member to a distal end of the outer tubular member and including a hub and a second magnet directly attached to the inner tubular member, the inner tubular member slidably disposed within the outer tubular member, the inner tubular member physically attached to and mechanically driven by the driveshaft during use of the tool with the handpiece, wherein a force is created between the first magnet and the second magnet when the inner tubular member is slidably disposed within the outer tubular member.

2. The tool of claim 1 wherein the force comprises an attractive force.

3. The tool of claim 2 wherein the attractive force creates a preload force between the inner tubular member and the outer tubular member.

4. The tool of claim 1 wherein the force comprises an opposing force.

5. The tool of claim 4 wherein the opposing force creates a preload force between the inner tubular member and the driveshaft upon engagement of the inner tubular member and the driveshaft.

6. The tool of claim 1 wherein the first magnet and the second magnet have different polarities.

7. The tool of claim 1 wherein the first magnet and the second magnet have same polarities.

8. The tool of claim 1 wherein an air gap exists between the first magnet and the second magnet.

9. The tool of claim 8 wherein the air gap is between about 0.001 inches and about 0.300 inches.

10. The tool of claim 1 wherein the first magnet is coupled to the outer tubular member.

11. The tool of claim 10 wherein the first magnet is coupled to a hub of the outer tubular member.

12. The tool of claim 1 wherein the second magnet is coupled to the inner tubular member.

13. The tool of claim 12 wherein the second magnet is coupled to the hub of the inner tubular member.

14. The tool of claim 1 wherein the inner tubular member and the outer tubular member both comprise magnetic material.

15. The tool of claim 14 wherein a hub of the inner tubular member and a hub of the outer tubular member both comprise magnetic material.

16. The tool of claim 15 wherein the magnetic material of the hub of the inner tubular member and the magnetic material of the hub of the outer tubular member have same polarities.

17. The tool of claim 15 wherein the magnetic material of the hub of the inner tubular member and the magnetic material of the hub of the outer tubular member have different polarities.

18. The cutting tool of claim 1 wherein the first magnet faces the second magnet and is axially spaced from it.

19. A surgical cutting tool for use with a handpiece, the handpiece including a drive shaft, the cutting tool comprising:
   a one-piece outer tubular member extending from a proximal end of the outer tubular member to a distal end of the outer tubular member, the outer tubular member including a cutting window formed within the distal end of the outer tubular member and a first magnet directly attached to the outer tubular member, the first magnet being a single magnet; and a one-piece inner tubular member extending from a proximal end of the inner tubular member to a distal end of the inner tubular member and including a hub and a second magnet directly attached to the inner tubular member, the inner tubular member slidably disposed within the outer tubular member, the inner tubular member physically attached to and mechanically driven by the driveshaft during use of the tool with the handpiece, wherein a force is created between the first magnet and the second magnet when the inner tubular member is slidably disposed within the outer tubular member.

20. The cutting tool of claim 19 wherein a planar face of the first magnet faces a planar face of the second magnet and is axially spaced from it.

21. A surgical instrument comprising:
an outer tubular member consisting of one-piece extending from a proximal end of the outer tubular member to a distal end of the outer tubular member and including a cutting window formed within the distal end of the outer tubular member;
a one-piece inner tubular member extending from a proximal end of the inner tubular member to a distal end of the inner tubular member, the inner tubular member including a first magnet directly attached to the inner tubular member and a hub directly attached to the inner tubular member including a drive tang integral with and extending from the hub of the inner tubular member, the inner tubular member slidably disposed within the outer tubular member; and
a separate handpiece including a second magnet directly attached to the handpiece, the handpiece for housing of the outer and inner tubular members, the handpiece including a driveshaft, the inner tubular member coupled to the driveshaft by physical engagement to be driven by the driveshaft,
wherein the first magnet and the second magnet are relatively arranged to provide an axially directed force between the inner tubular member and the handpiece to locate the inner tubular member within the hand piece.

22. The cutting tool of claim 21 wherein the force is an opposing force.

23. The cutting tool of claim 22 wherein the opposing force creates a preload force between the inner tubular member and the outer tubular member.

24. The cutting tool of claim 21 wherein the force is an attractive force.

25. The cutting tool of claim 24 wherein the attractive force creates a preload force between the inner tubular member and the hand piece.

26. The cutting tool of claim 21 wherein the magnet on the outer tubular member and the magnet on the inner tubular member comprise same polarities.

27. The cutting tool of claim 21 wherein the outer tubular member comprises a retention feature, the retention feature creating a coupling between the outer tubular member and the inner tubular member.

28. The cutting tool of claim 21 wherein an air gap exists between the magnet of the inner tubular member and the magnet of the hand piece.

29. The cutting tool of claim 28 wherein the air gap is between about 0.001 inches and about 0.300 inches.

30. The cutting tool of claim 21 wherein the first magnet faces the second magnet and is axially spaced from it.

31. A cutting tool comprising:
a one-piece outer tubular member extending from a proximal end of the outer tubular member to a distal end of the outer tubular member including a hub, a cutting member formed within the distal end of the outer tubular member, and a first magnet directly attached to the outer tubular member; and
a one-piece inner tubular member extending from a proximal end of the inner tubular member to a distal end of the inner tubular member, the inner tubular member including a hub having a drive tang attached to and extending from the hub of the inner tubular member and a second magnet directly attached to the inner tubular member, the inner tubular member slidably disposed within the outer tubular member for continuous rotation relative to the outer tubular member, wherein the drive tang of the inner tubular member hub is proximal to the outer tubular member hub,
wherein the first magnet and the second magnet are relatively arranged to provide an axially directed preload force between the inner tubular member and the outer tubular member.

32. The cutting tool of claim 31 wherein a planar face of the first magnet faces a planar face of the second magnet and is axially spaced from it.

33. The cutting tool of claim 31 wherein the first and second magnets both define through holes.

34. The cutting tool of claim 31 wherein the inner tubular member is continuously rotated in a single direction.

35. A surgical instrument comprising:
a one-piece outer tubular member extending from a proximal end of the outer tubular member to a distal end of the outer tubular member including a hub directly attached to a proximal end of the outer tubular member, a first magnet, and a cutting window formed within the distal end of the outer tubular member, the first magnet directly attached to the outer tubular member;
a one-piece inner tubular member extending from a proximal end of the inner tubular member to a distal end of the inner tubular member including a hub directly attached to a proximal end of the inner tubular member and a second magnet directly attached to the inner tubular member, the inner tubular member slidably disposed within the outer tubular member, the first magnet and the second magnet cooperating to retain the inner tubular member within the outer tubular member, the inner tubular member having a cutting surface opposite the cutting window; and
a handpiece including a drive shaft, the inner tubular member coupled to the driveshaft by physical engagement to be driven by the driveshaft,
wherein the cutting window of the outer tubular member and the cutting surface of the inner tubular member cooperate to cut tissue during surgery when only a rotational force is applied to the inner member by the drive shaft.

36. The cutting tool of claim 35 wherein the first magnet faces the second magnet and is axially spaced from it.

37. A cutting tool for use with a handpiece, the handpiece including a drive shaft, the cutting tool comprising:
a one-piece outer tubular member extending from a proximal end of the outer tubular member to a distal end of the outer tubular member including a cutting window formed within the distal end of the outer tubular member and a first magnet directly attached to the outer tubular member; and
a one-piece inner tubular member extending from a proximal end of the inner tubular member to a distal end of the inner tubular member including a hub and a second magnet directly attached to the inner tubular member, the inner tubular member slidably disposed within the outer tubular member, the inner tubular member physically attached to and driven by the driveshaft during use of the tool with the handpiece, wherein an axially directed preload force is created between the first magnet and the second magnet when the inner tubular member is slidably disposed within the outer tubular member.

38. The cutting tool of claim 37 wherein a planar face of the first magnet faces a planar face of the second magnet and is axially spaced from it.

39. A cutting tool for use with a handpiece, the handpiece including a drive shaft, the cutting tool comprising:
   a one-piece outer tubular member extending from a proximal end of the outer tubular member to a distal end of the outer tubular member including a cutting window formed within the distal end of the outer tubular member and a first magnet directly attached to the outer tubular member; and
   a one-piece inner tubular member extending from a proximal end of the inner tubular member to a distal end of the inner tubular member including a hub and a second magnet directly attached to the inner tubular member, the inner tubular member slidably disposed within the outer tubular member, the inner tubular member physically attached to and mechanically driven by the driveshaft during use of the tool with the handpiece, wherein the first magnet and the second magnet are relatively arranged to provide an axially directed preload force between the inner tubular member and the outer tubular member, the inner tubular member and the outer tubular member both received within the handpiece.

40. The cutting tool of claim 39 wherein the first magnet faces the second magnet and is axially spaced from it.

* * * * *